United States Patent [19]

Monia

[11] Patent Number: 5,981,731
[45] Date of Patent: Nov. 9, 1999

[54] ANTISENSE OLIGONUCLEOTIDE MODULATION OF B-RAF GENE EXPRESSION

[75] Inventor: Brett P. Monia, La Costa, Calif.

[73] Assignee: Isis Pharmaceuticals, Inc., Carlsbad, Calif.

[21] Appl. No.: 08/888,982

[22] Filed: Jul. 7, 1997

Related U.S. Application Data

[63] Continuation-in-part of application No. 08/756,806, filed as application No. PCT/US95/07111, May 31, 1995, which is a continuation-in-part of application No. 08/250,856, May 31, 1994, Pat. No. 5,563,255.

[51] Int. Cl.$^6$ ............................ C07H 21/00; A61K 31/70
[52] U.S. Cl. .............................................. 536/24.5; 514/44
[58] Field of Search ........................ 435/6, 375; 514/44; 536/24.31, 24.5

[56] References Cited

U.S. PATENT DOCUMENTS

| | | | |
|---|---|---|---|
| 5,034,506 | 7/1991 | Summerton et al. | 528/391 |
| 5,138,045 | 8/1992 | Cook et al. | 536/24.5 |
| 5,218,105 | 6/1993 | Cook et al. | 536/25.31 |
| 5,378,825 | 1/1995 | Cook et al. | 536/25.34 |
| 5,459,255 | 10/1995 | Cook et al. | 536/27.13 |
| 5,563,255 | 10/1996 | Monia et al. | 536/24.31 |
| 5,585,479 | 12/1996 | Hoke et al. | 536/24.5 |
| 5,591,721 | 1/1997 | Agrawal et al. | 514/44 |
| 5,744,362 | 4/1998 | Monia et al. | 435/375 |

FOREIGN PATENT DOCUMENTS

| | | |
|---|---|---|
| 92/20823 | 11/1992 | WIPO . |
| 93/04170 | 3/1993 | WIPO . |
| 93/06248 | 4/1993 | WIPO . |
| 94/23755 | 10/1994 | WIPO . |
| 94/26764 | 11/1994 | WIPO . |

OTHER PUBLICATIONS

Gewirtz et al. Facilitating oligonucleotide delivery: Helping antisense deliver on its promise. Proc. Natl. Acad. Sci. USA 93: 3161–3163, Apr. 1996.

Inoue et al. Sequence–dependent hydrolysis of RNA using modified oligonucleotide splints and RNAse H. FEBS Letts. 215(2): 327–330, May 1987.

Milligan et al. Current concpts in antisense drug design. J. Med. Chem. 36(14): 1923–1937, Jul. 1993.

Milner et al. Selecting effective antisense reagents on combinatorial oligonucleotide arrays. Nature Biotechnol. 15: 537–541, Jun. 1997.

Ahmad et al., "Antisense Expression of Protein Kinase Cα Inhibits the Growth and Tumorigenicity of Human Glioblastoma Cells", *Neurosurg.*, 1994, 35, 904–908.

*Catalog of Products for DNA Research*, Glen Research, Sterling VA, 1993, p. 21.

Chiang et al., "Antisense Oligonucleotides Inhibit Intercellular Adhesion Molecule 1 Expression by Two Distinct Mechanisms", *J. Biol. Chem.*, 1991, 266, 18162–18171.

De Mesmaeker et al., "Antisense Oligonucleotides", *Acc. Chem. Res.*, 1995, 28, 366–374.

Gebeyehu, G. et al., "Novel biotinylated nucleotide—analogs for labeling and colorimetric detection of DNA", *Nucl. Acids Res.*, 1987, 15, 4513–4534.

Kabanov et al., "A new class of antivirals: antisense oligonucleotides combined with a hydrophobic substituent effectively inhibit influenza virus reproduction and synthesis of virus–specific proteins in MDCK cells", *FEBS Lett.*, 1990, 259, 327–330.

Kawasaki et al., "Uniformly Modified 2'–Deoxy-2'–fluoro Phosphorothioate Oligonucleotides as Nuclease–Resistant Antisense Compounds with High Affinity and Specificity for RNA Targets ", *J. Med. Chem.*, 1993, 36, 831–841.

Kingston, R.E., in *Current Protocols in Molecular Biology*, (F.M. Ausubel et al., eds.), John Wiley and Sons, NY, 1993.

Kornberg, A., *DNA Replication*, W.H. Freeman & Co., San Francisco, 1980, pp. 75–77.

Letsinger et al., "Cholesteryl–conjugated oligonucleotides: Synthesis, properties, and activity as inhibitors of replication of human immunodeficiency virus in cell culture", *Proc. Natl. Acad. Sci. USA*, 1989, 86, 6553–6556.

Maister, P., "Isis' Antisense Drug Shows Promise for Retinitis", *BioWorld Today*, Apr. 29, 1994, p.3.

Manoharan et al., "Cholic Acid–Oligonucleotide Conjugates for Antisense Applications", *Bioorg. Med. Chem. Let.*, 1994, 4, 1053–1060.

Manoharan et al., "Chemical Modifications to Improve Uptake and Bioavailability of Antisense Oligonucleotides ", *Ann. N.Y. Acad. Sci.*, 1992, 660, 306–309.

Manoharan et al., "Introduction of a Lipophilic Thioether Tether in the Minor Groove of Nucleic Acids for Antisense Applications", *Bioorg. Med. Chem. Let.*, 1993, 3, 2765–2770.

Manoharan et al., "Oligonucleotide Conjugates: Alteration of the Pharmacokinetic Properties of Antisense Agents", *Nucleosides & Nucleotides*, 1995, 14, 969–973.

Manoharan et al., "Lipidic Nucleic Acids", *Tetrahedron Lett.*, 1995, 36, 3651–3654.

Marais et al., "Differential Regulation of Raf–1, A–Raf and B–Raf by Oncogenic Ras and Tyrosine Kinases", *J. Biol. Chem.* 1997, 272, 4378–4383.

Martin, P., "Ein neuer Zugang zu 2'–O –Alkylribonucleosiden und Eigenschaften deren Oligonucleotide", *Helv. Chim. Acta*, 1995, 78, 486–504.

(List continued on next page.)

*Primary Examiner*—George C. Elliott
*Assistant Examiner*—Thomas G. Larson
*Attorney, Agent, or Firm*—Law Offices of Jane Massey Licata

[57] ABSTRACT

Oligonucleotides are provided which are targeted to nucleic acids encoding human raf and capable of inhibiting raf expression. Methods of inhibiting the expression of human raf using oligonucleotides of the invention are also provided. The present invention further comprises methods of preventing or inhibiting hyperproliferation of cells and methods of treating abnormal proliferative conditions which employ oligonucleotides of the invention.

6 Claims, 4 Drawing Sheets

OTHER PUBLICATIONS

Monia et al., "Antitumor activity of a phosphorothioate antisense oligodeoxynucleotide targeted against C–raf kinase", *Nature Med.,* 1996, 2, 668–675.

Nielsen et al., "Sequence–Selective Recognition of DNA by Strand Displacement with a Thymine–Substituted Polyamide", *Science,* 1991, 254, 1497–1500.

Oberhauser et al., "Effective incorporation of 2'–O–methyl–oligoribonucleotides into liposomes and enhanced cell association through modification with thiocholesterol", *Nucl. Acids Res.,* 1992, 20, 533–538.

Rapp et al., *The Oncogene Handbook,* E.P. Reddy, A.M Skalka and T. Curran, eds., Elsevier Science Publishers, New York, 1988, pp. 213–253.

Riedel et al., "The mitogenic response of T cells to interleukin–2 requires Raf–1", *Eur. J. Immunol.* 1993, 23, 3146–3150.

Sanghvi, Y.S., in Crooke, S.T. and Lebleu, B., eds., *Antisense Research and Applications,* CRC Press, Boca Raton, 1993, pp. 276–278.

Sanghvi et al., "Antisense oligodeoxynucleotides: synthesis, biophysical and biological evaluation of oligodeoxynucleotides containing modified pyrimidines", *Nucl. Acids Res.,* 1993, 21, 3197–3203.

Saison–Behmoaras et al., "Short modified antisense oligonucleotides directed against Ha–ras point mutation induce selective cleavage of the mRNA and inhibit T24 cells proliferation", *EMBO J.,* 1991, 10, 1111–1118.

Svinarchuk et al., "Inhibition of HIV proliferation in NT–4 cells by antisense oligonucleotide conjugated to lipophilic groups", *Biochimie,* 1993, 75, 49–54.

Sambrook et al., *Molecular Cloning. A Laboratory Manual,* Cold Spring Harbor Laboratory Press, 1989, vol. 2, p. 10.59, 11.31–11.32.

Tornkvist et al., "Inhibition of Raf–1 Kinase Expression Abolishes Insulin Stimulation of DNA Synthesis in H4IIE Hepatoma Cells", *J. Biol. Chem.* 1994, 269, 13919–13921.

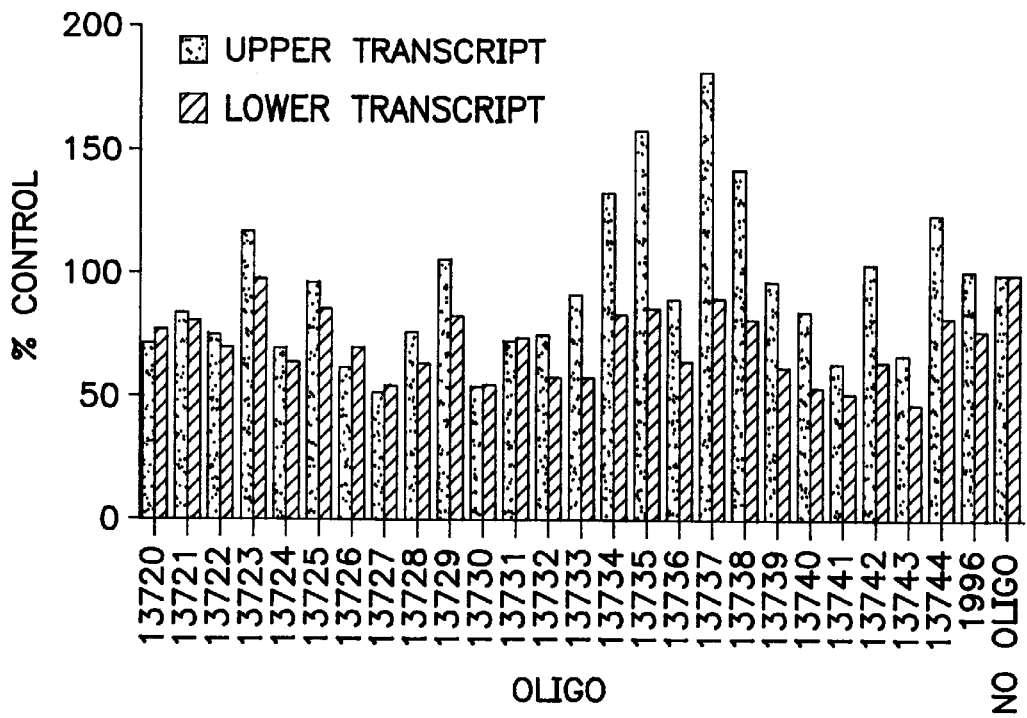
FIG. IA
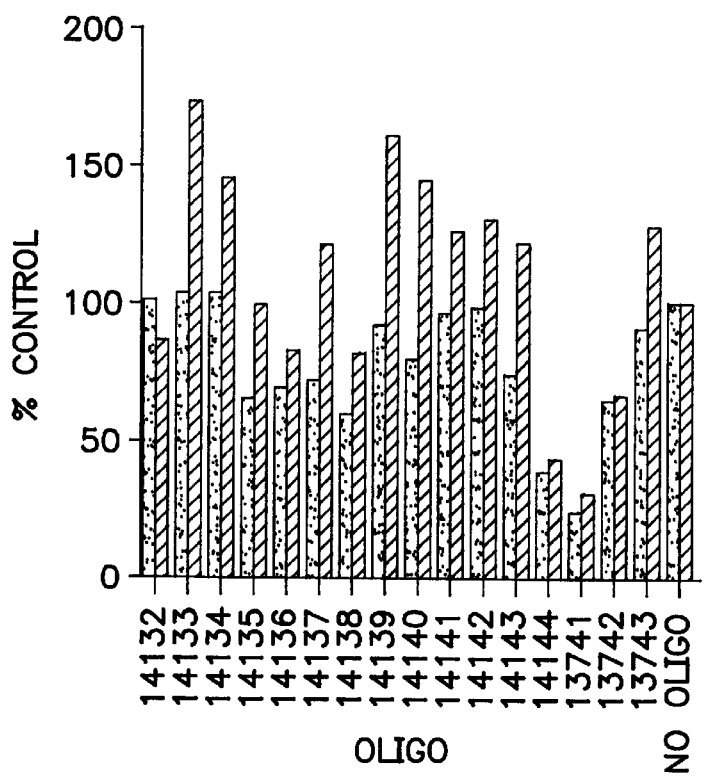
FIG. IB

SEQUENCE LISTING (1) GENERAL INFORMATION:

(iii) NUMBER OF SEQUENCES: 42

(2) INFORMATION FOR SEQ ID NO: 1:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 1:

ATTTTGAAGG AGACGGACTG                                           20

(2) INFORMATION FOR SEQ ID NO: 2:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 2:

TGGATTTTGA AGGAGACGGA                                           20

(2) INFORMATION FOR SEQ ID NO: 3:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 3:

CGTTAGTTAG TGAGCCAGGT                                           20

(2) INFORMATION FOR SEQ ID NO: 4:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 4:

ATTTCTGTAA GGCTTTCACG                                           20

(2) INFORMATION FOR SEQ ID NO: 5:

(i) SEQUENCE CHARACTERISTICS:
          (A) LENGTH: 20
          (B) TYPE: Nucleic Acid
          (C) STRANDEDNESS: Single
          (D) TOPOLOGY: Linear (iv) ANTI-SENSE: Yes (xi) SEQUENCE DESCRIPTION: SEQ ID NO: 5:

CCCGTCTACC AAGTGTTTTC 20

(2) INFORMATION FOR SEQ ID NO: 6:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

AATCTCCCAA TCATCACTCG 20

(2) INFORMATION FOR SEQ ID NO: 7:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

TGCTGAGGTG TAGGTGCTGT 20

(2) INFORMATION FOR SEQ ID NO: 8:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

TGTAACTGCT GAGGTGTAGG 20

(2) INFORMATION FOR SEQ ID NO: 9:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

TGTCGTGTTT TCCTGAGTAC 20

(2) INFORMATION FOR SEQ ID NO: 10:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

AGTTGTGGCT TTGTGGAATA 20

(2) INFORMATION FOR SEQ ID NO: 11:

```
        (i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 11:

ATGGAGATGG TGATACAAGC                                                      20

(2) INFORMATION FOR SEQ ID NO: 12:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 12:

GGATGATTGA CTTGGCGTGT                                                      20

(2) INFORMATION FOR SEQ ID NO: 13:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 13:

AGGTCTCTGT GGATGATTGA                                                      20

(2) INFORMATION FOR SEQ ID NO: 14:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 14:

ATTCTGATGA CTTCTGGTGC                                                      20

(2) INFORMATION FOR SEQ ID NO: 15:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 15:

GCTGTATGGA TTTTTATCTT                                                      20

(2) INFORMATION FOR SEQ ID NO: 16:

(i) SEQUENCE CHARACTERISTICS:
            (A) LENGTH: 20
            (B) TYPE: Nucleic Acid
            (C) STRANDEDNESS: Single
            (D) TOPOLOGY: Linear
```

(iv) ANTI-SENSE: Yes (xi) SEQUENCE DESCRIPTION: SEQ ID NO: 16:

TACAGAACAA TCCCAAATGC                                   20

(2) INFORMATION FOR SEQ ID NO: 17:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 17:

ATCCTCGTCC CACCATAAAA                                   20

(2) INFORMATION FOR SEQ ID NO: 18:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 18:

CTCTCATCTC TTTTCTTTTT                                   20

(2) INFORMATION FOR SEQ ID NO: 19:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 19:

GTCTCTCATC TCTTTTCTTT                                   20

(2) INFORMATION FOR SEQ ID NO: 20:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 20:

CCGATTCAAG GAGGGTTCTG                                   20

(2) INFORMATION FOR SEQ ID NO: 21:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 21:

TGGATGGGTG TTTTTGGAGA                                                20

(2) INFORMATION FOR SEQ ID NO: 22:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

CTGCCTGGAT GGGTGTTTTT                                                20

(2) INFORMATION FOR SEQ ID NO: 23:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

GGACAGGAAA CGCACCATAT                                                20

(2) INFORMATION FOR SEQ ID NO: 24:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 24:

CTCATTTGTT TCAGTGGACA                                                20

(2) INFORMATION FOR SEQ ID NO: 25:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 25:

TCTCTCACTC ATTTGTTTCA                                                20

(2) INFORMATION FOR SEQ ID NO: 26:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 26:

ACTCTCTCAC TCATTTGTTT                                                20

(2) INFORMATION FOR SEQ ID NO: 27:

```
    (i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 27:

GAACTCTCTC ACTCATTTGT                                                    20

(2) INFORMATION FOR SEQ ID NO: 28:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

TCCTGAACTC TCTCACTCAT                                                    20

(2) INFORMATION FOR SEQ ID NO: 29:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 29:

TTGCTACTCT CCTGAACTCT                                                    20

(2) INFORMATION FOR SEQ ID NO: 30:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 30:

TTTGTTGCTA CTCTCCTGAG                                                    20

(2) INFORMATION FOR SEQ ID NO: 31:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

CTTTTGTTGC TACTCTCCTG                                                    20

(2) INFORMATION FOR SEQ ID NO: 32:

(i) SEQUENCE CHARACTERISTICS:
        (A) LENGTH: 20
        (B) TYPE: Nucleic Acid
        (C) STRANDEDNESS: Single
        (D) TOPOLOGY: Linear
```

(iv) ANTI-SENSE: Yes (xi) SEQUENCE DESCRIPTION: SEQ ID NO: 32:

GCTACTCTCC TGAACTCTCT                                                  20

(2) INFORMATION FOR SEQ ID NO: 33:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 33:

TTCCTTTTGT TGCTACTCTC                                                  20

(2) INFORMATION FOR SEQ ID NO: 34:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 34:

ATTTATTTTC CTTTTGTTGC                                                  20

(2) INFORMATION FOR SEQ ID NO: 35:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 35:

ATATGTTCAT TTATTTTCCT                                                  20

(2) INFORMATION FOR SEQ ID NO: 36:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 36:

TTTATTTTCC TTTTGTTGCT                                                  20

(2) INFORMATION FOR SEQ ID NO: 37:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 37:

TGTTCATTTA TTTTCCTTTT                                                  20

(2) INFORMATION FOR SEQ ID NO: 38:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 38:

ATTTAACATA TAAGCAAACA                                          20

(2) INFORMATION FOR SEQ ID NO: 39:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 39:

CTGCCTGGTA CCCTGTTTTT                                          20

(2) INFORMATION FOR SEQ ID NO: 40:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 40:

CTGCCTGGAA GGGTGTTTTT                                          20

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 41:

CTGCCTGGTA CGGTGTTTTT                                          20

(2) INFORMATION FOR SEQ ID NO: 42:

(i) SEQUENCE CHARACTERISTICS:
        (A) LENGTH: 2510
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 42:

cgcctcccgg cccccuccc gcccgacagc ggccgctcgg gccccggctc          50
tcggttataa gatggcggcg ctgagcggtg gcggtggtgg cggcgcggag         100
ccgggccagg ctctgttcaa cggggacatg gagcccgagg ccggcgccgg         150

```
ccggcccgcg gcctcttcgg ctgcggaccc tgccattccg gaggaggtgt         200
ggaatatcaa acaaatgatt aagttgacac aggaacatat agaggccta          250 ttggacaaat ttggtgggga gcataatcca ccatcaatat atctggaggc         300
ctatgaagaa tacaccagca agctagatgc actccaacaa agagaacaac         350
agttattgga atctctgggg aacggaactg attttctgt ttctagctct          400 gcatcaatgg ataccgttac atcttcttcc tcttctagcc tttcagtgct         450
accttcatct ctttcagttt ttcaaaatcc cacagatgtg gcacggagca         500
accccaagtc accacaaaaa cctatcgtta gagtcttcct gcccaacaaa         550
cagaggacag tggtacctgc aaggtgtgga gttacagtcc gagacagtct         600
aaagaaagca ctgatgatga gaggtctaat cccagagtgc tgtgctgttt         650
acagaattca ggatggagag aagaaaccaa ttggttggga cactgatatt         700
tcctggctta ctgagaaga attgcatgtg aagtgttgg agaatgttcc           750 acttacaaca cacaactttg tacgaaaaac gttttcacc ttagcatttt          800 gtgacttttg tcgaaagctg cttttccagg gtttccgctg tcaaacatgt         850
ggttataaat ttcaccagcg ttgtagtaca gaagttccac tgatgtgtgt         900
taattatgac caacttgatt tgctgtttgt ctccaagttc tttgaacacc         950
acccaatacc acaggaagag gcgtccttag cagagactgc cctaacatct         1000
ggatcatccc cttccgcacc cgcctcggac tctattgggc cccaaattct         1050
caccagtccg tctccttcaa aatccattcc aattccacag cccttccgac         1100
cagcagatga agatcatcga aatcaatttg ggcaacgaga ccgatcctca         1150
tcagctccca atgtgcatat aaacacaata gaacctgtca atattgatga         1200
cttgattaga gaccaaggat ttcgtggtga tggaggatca accacaggtt         1250
tgtctgctac ccccccctgcc tcattacctg gctcactaac taacgtgaaa        1300
gccttacaga aatctccagg acctcagcga gaaaggaagt catcttcatc         1350
ctcagaagac aggaatcgaa tgaaaacact tggtagacgg gactcgagtg         1400
atgattggga gattcctgat gggcagatta cagtgggaca aagaattgga         1450
tctggatcat ttggaacagt ctacaaggga agtggcatg gtgatgtggc          1500 agtgaaaatg ttgaatgtga cagcacctac acctcagcag ttacaagcct         1550
tcaaaaatga agtaggagta tcaggaaaa cacgacatgt gaatatccta          1600
ctcttcatgg gctattccac aaagccacaa ctggctattg ttacccagtg         1650
gtgtgagggc tccagcttgt atcaccatct ccatatcatt gagaccaaat         1700
ttgagatgat caaacttata gatattgcac gacagactgc acagggcatg         1750
gattacttac acgccaagtc aatcatccac agagacctca agagtaataa         1800
tatatttctt catgaagacc tcacagtaaa aataggtgat tttggtctag         1850
ctacagtgaa atcgatgg agtgggtccc atcagtttga acagttgtct           1900
ggatccattt tgtggatggc accagaagtc atcagaatgc aagataaaa          1950 tccatacagc tttcagtcag atgtatatgc atttgggatt gttctgtatg         2000
aattgatgac tggacagtta ccttattcaa acatcaacaa cagggaccag         2050 ataatttta tggtgggacg aggataccctg tctccagatc tcagtaaggt         2100
acggagtaac tgtccaaaag ccatgaagag attaatggca gagtgcctca        2150
```

-continued

| | | | | |
|---|---|---|---|---|
| aaaagaaaag | agatgagaga | ccactctttc | cccaaattct | cgcctctatt | 2200 |
| gagctgctgg | cccgctcatt | gccaaaaatt | caccgcagtg | catcagaacc | 2250 |
| ctccttgaat | cgggctggtt | tccaaacaga | ggattttagt | ctatatgctt | 2300 |
| gtgcttctcc | aaaacaccc | atccaggcag | ggggatatgg | tgcgtttcct | 2350 |
| gtccactgaa | acaaatgagt | gagagagttc | aggagagtag | caacaaaagg | 2400 |
| aaaataaatg | aacatatgtt | tgcttatatg | ttaaattgaa | taaaatactc | 2450 |
| tcttttttt | taaggtggaa | aaaaaaaaaa | aaaaaaaaaa | aaaaaaaaaa | 2500 |
| aaaaaaaccc | | | | | 2510 |

ANTISENSE OLIGONUCLEOTIDE MODULATION OF B-RAF GENE EXPRESSION

This application is a continuation-in-part of U.S. patent application Ser. No. 08/756,806, filed Nov. 26, 1996, which is a U.S. National phase equivalent of PCT/US95/07111 filed May 31, 1995, which in turn is a foreign filing and continuation-in part of Ser. No. 08/250,856 filed May 31, 1994, issued as U.S. Pat. No. 5,563,255. Each of these applications is assigned to the assignee of the present invention and is incorporated herein in its entirety.

FIELD OF THE INVENTION

This invention relates to compositions and methods for modulating expression of raf, a naturally present cellular protein which has been implicated in abnormal cell proliferation and tumor formation. Compositions and methods for modulating B-raf are provided. This invention is also directed to methods for inhibiting hyperproliferation of cells; these methods can be used diagnostically or therapeutically. Furthermore, this invention is directed to treatment of conditions associated with expression of the raf gene.

BACKGROUND OF THE INVENTION

Alterations in the cellular genes which directly or indirectly control cell growth and differentiation are considered to be the main cause of cancer. The raf gene family includes three highly conserved genes termed A-, B- and c-raf (also called raf-1). Raf genes encode protein kinases that are thought to play important regulatory roles in signal transduction processes that regulate cell proliferation. Expression of the c-raf protein is believed to play a role in abnormal cell proliferation since it has been reported that 60% of all lung carcinoma cell lines express unusually high levels of c-raf mRNA and protein. Rapp et al., *The Oncogene Handbook*, E. P. Reddy, A. M Skalka and T. Curran, eds., Elsevier Science Publishers, New York, 1988, pp. 213–253. B-raf is strongly activated by oncogenic ras. Marais et al., (1997) *J. Biol. Chem.* 272: 4378–4383.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases.

Antisense oligonucleotides have been safely administered to humans and clinical trials of several antisense oligonucleotide drugs, targeted both to viral and cellular gene products, are presently underway. The phosphorothioate oligonucleotide, ISIS 2922, has been shown to be effective against cytomegalovirus retinitis in AIDS patients. *BioWorld Today*, Apr. 29, 1994, p 3. The oligonucleotide drug, ISIS5132/CGP69846A, a phosphorothioate deoxyoligonucleotide targeted to human c-raf, is currently in Phase I clinical trials. This compound has shown potent antitumor activity in a variety of animal models of human tumors. It is thus established that oligonucleotides in general, and those targeted to raf in particular, can be useful therapeutic instrumentalities and can be useful in treatment of cells and animal subjects, especially humans.

Antisense oligonucleotide inhibition of gene expression has proven to be a useful tool in understanding the roles of raf gene products. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., *Eur. J. Immunol.* 1993, 23, 3146–3150. Rapp et al. have disclosed expression vectors containing a raf gene in an antisense orientation downstream of a promoter, and methods of inhibiting raf expression by expressing an antisense Raf gene or a mutated Raf gene in a cell. WO application 93/04170. An antisense oligodeoxyribonucleotide complementary to codons 1–6 of murine c-Raf has been used to abolish insulin stimulation of DNA synthesis in the rat hepatoma cell line H4IIE. Tornkvist et al., *J. Biol. Chem.* 1994, 269, 13919–13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation.

Denner et al. disclose antisense polynucleotides hybridizing to the gene for raf, and processes using them. WO 94/15645. Oligonucleotides hybridizing to human and rat raf sequences are disclosed.

Iversen et al. disclose heterotypic antisense oligonucleotides complementary to raf which are able to kill ras-activated cancer cells, and methods of killing raf-activated cancer cells. Numerous oligonucleotide sequences are disclosed, none of which are actually antisense oligonucleotide sequences. WO 94/23755.

SUMMARY OF THE INVENTION

The present invention provides oligonucleotides which are targeted to nucleic acids encoding human raf, particularly B-raf, and which are capable of inhibiting raf expression. The oligonucleotides of the invention are believed to be useful both diagnostically and therapeutically, and are believed to be particularly useful in the methods of the present invention.

The present invention also comprises methods of inhibiting the expression of human raf. These methods are believed to be useful both therapeutically and diagnostically as a consequence of the association between raf expression and hyperproliferation. These methods are also useful as tools, for example for detecting and determining the role of raf expression in various cell functions and physiological processes and conditions and for diagnosing conditions associated with raf expression.

The present invention also comprises methods of inhibiting hyperproliferation of cells using oligonucleotides of the invention. These methods are believed to be useful, for example in diagnosing raf-associated cell hyperproliferation. Methods of treating abnormal proliferative conditions are also provided. These methods employ the oligonucleotides of the invention. These methods are believed to be useful both therapeutically and as clinical research and diagnostic tools.

DESCRIPTION OF THE DRAWINGS

FIGS. 1A and 1B are a set of bar graphs showing initial screens of oligonucleotides targeted to human B-raf. FIG. 1A shows results for oligonucleotides ISIS 13720–13744. mRNA levels for both lower transcript (solid gray bars) and upper transcript (speckled bars) are shown. FIG. 1B shows results for oligonucleotides 14132–14144, along with 13741, 13742 and 13743. mRNA levels for both upper transcript (solid gray bars) and lower transcript (speckled bars) are shown.

FIG. 2A shows a dose-response curve for inhibition of the upper B-raf transcript. FIG. 2B shows a dose-response curve for inhibition of the lower B-raf transcript.

FIG. 3A shows a dose-response curve for inhibition of the upper B-raf transcript. FIG. 3B shows a dose-response curve for inhibition of the lower B-raf transcript.

FIG. 4A shows a dose-response curve for inhibition of the upper B-raf transcript. FIG. 4B shows a dose-response curve for inhibition of the lower B-raf transcript.

DETAILED DESCRIPTION OF THE INVENTION

Figure 2A:
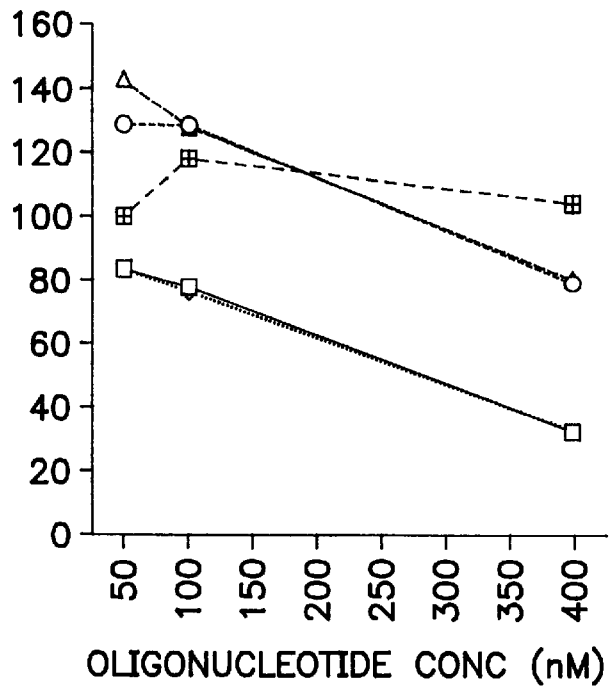
FIGS. 2A and 2B are a set of line graphs showing dose-response curves for reduction of B-raf mRNA levels in human A549 tumor cells by phosphorothioate oligodeoxynucleotides 13741 (open squares), 14144 (diamonds), 14529 (circles), 14530 (triangles) and 14531 (crosshatched squares) after a 4-hour treatment in the presence of lipofectin. Results are normalized to G3PDH and expressed as a percent of control.

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. The raf genes are members of a gene family which encode related proteins termed A-, B- and c-raf. Raf genes code for highly conserved serine-threonine-specific protein kinases which are known to bind to the ras oncogene. They are part of a signal transduction pathway believed to consist of receptor tyrosine kinases, p21 ras, Raf protein kinases, Mek1 (ERK activator or MAPKK) kinases and ERK (MAPK) kinases, which ultimately phosphorylate transcription factors. Signaling through this pathway can mediate differentiation, proliferation or oncogenic transformation in different cellular contexts. Marais et al., (1997) J. Biol. Chem. 272: 4378–4383. Thus, raf kinases are believed to play a fundamental role in the normal cellular signal transduction pathway, coupling a multitude of growth factors to their net effect, cellular proliferation. Because raf proteins are direct downstream effectors of ras protein function, therapies directed against raf kinases are believed to be useful in treatment of ras-dependent tumors. Monia et al. (1996) Nature Med. 2:668–675. The raf kinases are differentially regulated and expressed; c-raf, also known as raf-1, is the most thoroughly characterized and is expressed in all organs and in all cell lines that have been examined. A- and B-raf are highly expressed in urogenital and brain tissues, respectively. Because B-raf is highly expressed in neural tissues it was once thought to be limited to these tissues but it has since been found to be more widely expressed. Although all the raf kinases are bound by ras following ras stimulation, B-raf is most strongly activated (phosphorylated) by oncogenic ras, and may be the primary target of oncogenic ras in cell transformation. Marais et al., (1997) J. Biol. Chem. 272: 4378–4383.

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following angioplasty. The cellular signalling pathway of which raf is a part has also been implicated in inflammatory disorders characterized by T-cell proliferation (T-cell activation and growth), such as tissue graft rejection, endotoxin shock, and glomerular nephritis, for example.

It has now been found that elimination or reduction of raf expression may halt or reverse abnormal cell proliferation. This has been found even when levels of raf expression are not abnormally high. There is a great desire to provide compositions of matter which can modulate the expression of raf. It is greatly desired to provide methods of detection of nucleic acids encoding raf in cells, tissues and animals. It is also desired to provide methods of diagnosis and treatment of abnormal proliferative conditions associated with abnormal raf expression. In addition, kits and reagents for detection and study of nucleic acids encoding raf are desired. "Abnormal" raf expression is defined herein as abnormally high levels of expression of the raf protein, expression of an abnormal or mutant raf protein, or any level of raf expression in an abnormal proliferative condition or state.

The present invention employs oligonucleotides targeted to nucleic acids encoding raf. This relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding raf; in other words, the raf gene or mRNA expressed from the raf gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of raf gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In preferred embodiments of this invention, oligonucleotides are provided which are targeted to mRNA encoding B-raf. In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of the human B-raf mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with raf protein expression.

The present invention provides oligonucleotides for modulation of raf gene expression. Such oligonucleotides are targeted to nucleic acids encoding raf. Oligonucleotides and methods for modulation of B-raf are provided; however, compositions and methods for modulating expression of other forms of raf are also believed to have utility and are comprehended by this invention. As hereinbefore defined, "modulation" means either inhibition or stimulation. Inhibition of raf gene expression is presently the preferred form of modulation.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding raf) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase raf mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of raf gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. A discussion of antisense oligonucleotides and some desirable modifications can be found in De Mesmaeker et al., 1995, *Acc. Chem. Res.* 28:366–374.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$—$N(CH_3)$—O—$CH_2$ [known as a methylene (methylimino) or MMI backbone], $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones, wherein the native phosphodiester backbone is represented as O—P—O—$CH_2$). The amide backbones disclosed by De Mesmaeker et al. (1995, *Acc. Chem. Res.* 28:366–374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science,* 1991, 254, 1497).

Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy (also known in the art as O-alkyl-O-alkyl), substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl) or 2'-MOE] (Martin et al., *Helv. Chim. Acta,* 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Kornberg, A., *DNA Replication,* W. H. Freeman & Co., San Francisco, 1980, pp75–77; Gebeyehu, G., et al., 1987, *Nucl. Acids Res.* 15:4513). A "universal" base known in the art, e.g., inosine, may be included. 5-me-C substitutions have been shown to increase nucleic acid duplex stability by 0.6–1.2° C. (Sanghvi, Y. S., in Crooke, S. T. and Lebleu, B., eds., *Antisense Research and Applications,* CRC Press, Boca Raton, 1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA,* 1989, 86, 6553), cholic acid (Manoharan et al., *Bioorg. Med. Chem. Let.,* 1994, 4, 1053), a thioether, e.g., hexyl-S-tritylthiol (Manoharan et al., *Ann. N.Y. Acad. Sci.,* 1992, 660, 306; Manoharan et al., *Bioorg. Med. Chem. Let.,* 1993, 3, 2765), a thiocholesterol (Oberhauser et al., *Nucl. Acids Res.,* 1992, 20, 533), an aliphatic chain, e.g., dodecandiol or undecyl residues (Saison-Behmoaras et al., *EMBO J.,* 1991, 10, 111; Kabanov et al., *FEBS Lett.,* 1990, 259, 327; Svinarchuk et al., *Biochimie,* 1993, 75, 49), a phospholipid, a polyamine or a polyethylene glycol chain (Manoharan et al., *Nucleosides & Nucleotides,* 1995, 14, 969), or adamantane acetic acid (Manoharan et al., *Tetrahedron Lett.,* 1995, 36, 3651). Oligonucleotides comprising lipophilic moieties, and methods for preparing such oligonucleotides are known in the art, for example, U.S. Pat. No. 5,138,045, No. 5,218,105 and No. 5,459,255.

The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes chimeric oligonucleotides as hereinbefore defined.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

It has now been found that certain oligonucleotides targeted to portions of the B-raf mRNA are useful for inhibiting raf expression. Inhibition of B-raf expression using antisense oligonucleotides is believed to be useful for interfering with cell hyperproliferation. In the methods of the invention, tissues or cells are contacted with oligonucleotides. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of inhibiting hyperproliferation of cells and methods of preventing and treating abnormal proliferative conditions are provided. The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absorption and distribution characteristics. U.S. Pat. No. 5,591,721 (Agrawal et al.). Oligonucleotides with at least one 2'-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is Lipofectin (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on IC50's or EC50's in in vitro and in vivo animal studies. For example, given the molecular weight of compound (derived from oligonucleotide sequence and chemical structure) and an effective dose such as an IC50, for example (derived experimentally), a dose in mg/kg is routinely calculated.

The present invention is also suitable for diagnosing abnormal proliferative states in tissue or other samples from patients suspected of having a hyperproliferative disease such as cancer, psoriasis or blood vessel restenosis or atherosclerosis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish raf-associated, or, particularly, B-raf-associated tumors from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of raf expression. For example, radiolabeled oligonucleotides can be prepared by $^{32}$P labeling at the 5' end with polynucleotide kinase. Sambrook et al., *Molecular Cloning. A Laboratory Manual*, Cold Spring Harbor Laboratory Press, 1989, Volume 2, p. 10.59. Radiolabeled oligonucleotides are then contacted with tissue or cell samples suspected of raf expression and the sample is washed to remove unbound oligonucleotide. Radioactivity remaining in the sample indicates bound oligonucleotide (which in turn indicates the presence of raf) and can be quantitated using a scintillation counter or other routine means. Radiolabeled oligo can also be used to perform autoradiography of tissues to determine the localization, distribution and quantitation of raf expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing raf. Quantitation of the silver grains permits raf expression to be detected.

Analogous assays for fluorescent detection of raf expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 *Catalog of Products for DNA Research*, Glen Research, Sterling Va., p. 21).

Each of these assay formats is known in the art. One of skill could easily adapt these known assays for detection of raf expression in accordance with the teachings of the invention providing a novel and useful means to detect raf expression.

Oligonucleotide inhibition of B-raf expression

The oligonucleotides shown in Table 1 were designed using the Genbank B-raf sequence HUMBRAF (SEQ ID NO: 42 Genbank listings M95712;M95720;x54072), synthesized and tested for inhibition of B-raf mRNA expression in T24 bladder carcinoma cells or A549 lung carcinoma cells using a Northern blot assay.

TABLE 1

Human B-raf Kinase Antisense Oligonucleotides
(All are phosphorothioate oligodeoxynucleotides)

| Isis # | Sequence (5' → 3') | Site | SEQ ID NO: |
|---|---|---|---|
| 13720 | ATTTTGAAGGAGACGGACTG | coding | 1 |
| 13721 | TGGATTTTGAAGGAGACGGA | coding | 2 |
| 13722 | CGTTAGTTAGTGAGCCAGGT | coding | 3 |
| 13723 | ATTTCTGTAAGGCTTTCACG | coding | 4 |
| 13724 | CCCGTCTACCAAGTGTTTTC | coding | 5 |
| 13725 | AATCTCCCAATCATCACTCG | coding | 6 |
| 13726 | TGCTGAGGTGTAGGTGCTGT | coding | 7 |
| 13727 | TGTAACTGCTGAGGTGTAGG | coding | 8 |
| 13728 | TGTCGTGTTTTCCTGAGTAC | coding | 9 |
| 13729 | AGTTGTGGCTTTGTGGAATA | coding | 10 |
| 13730 | ATGGAGATGGTGATACAAGC | coding | 11 |
| 13731 | GGATGATTGACTTGGCGTGT | coding | 12 |
| 13732 | AGGTCTCTGTGGATGATTGA | coding | 13 |
| 13733 | ATTCTGATGACTTCTGGTGC | coding | 14 |
| 13734 | GCTGTATGGATTTTTATCTT | coding | 15 |
| 13735 | TACAGAACAATCCCAAATGC | coding | 16 |
| 13736 | ATCCTCGTCCCACCATAAAA | coding | 17 |
| 13737 | CTCTCATCTCTTTTCTTTTT | coding | 18 |
| 13738 | GTCTCTCATCTCTTTTCTTT | coding | 19 |
| 13739 | CCGATTCAAGGAGGGTTCTG | coding | 20 |
| 13740 | TGGATGGGTGTTTTTGGAGA | coding | 21 |
| 13741 | CTGCCTGGATGGGTGTTTTT | coding | 22 |
| 14144 | GGACAGGAAACGCACCATAT | coding | 23 |
| 14143 | CTCATTTGTTTCAGTGGACA | stop codon | 24 |
| 14142 | TCTCTCACTCATTTGTTTCA | stop codon | 25 |
| 14141 | ACTCTCTCACTCATTTGTTT | stop codon | 26 |
| 14140 | GAACTCTCTCACTCATTTGT | coding | 27 |
| 14139 | TCCTGAACTCTCTCACTCAT | coding | 28 |
| 14138 | TTGCTACTCTCCTGAACTCT | 3'UTR | 29 |
| 14137 | TTTGTTGCTACTCTCCTGAG | coding | 30 |
| 14136 | CTTTTGTTGCTACTCTCCTG | 3'UTR | 31 |
| 13742 | GCTACTCTCCTGAACTCTCT | 3'UTR | 32 |
| 14135 | TTCCTTTTGTTGCTACTCTC | 3'UTR | 33 |
| 14134 | ATTTATTTTCCTTTTGTTGC | coding | 34 |
| 14133 | ATATGTTCATTTATTTTCCT | coding | 35 |
| 13743 | TTTATTTTCCTTTTGTTGCT | 3'UTR | 36 |
| 13744 | TGTTCATTTATTTTCCTTTT | coding | 37 |
| 14132 | ATTTAACATATAAGCAAACA | coding | 38 |
| 14529 | CTGCCTGGTACCCTGTTTTT | 5 mismatch | 39 |
| 14530 | CTGCCTGGAAGGGTGTTTTT | 1 mismatch | 40 |
| 14531 | CTGCCTGGTACGGTGTTTTT | 3 mismatch | 41 |

There are multiple B-raf transcripts. The two most prevalent transcripts were quantitated after oligonucleotide treatment. These transcripts run at approximately 8.5 kb (upper transcript) and 4.7 kb (lower transcript) under the gel conditions used. Both transcripts are translated into B-raf protein in cells. In the initial screen, A549 cells were treated with oligonucleotides at a concentration of 200 nM oligonucleotide for four hours in the presence of lipofectin. Results were normalized and expressed as a percent of control. A graph showing oligonucleotide effect on levels of B-raf mRNA (both upper and lower transcripts) is shown in FIG. 1 (panels A and B). In this initial screen, oligonucleotides giving a reduction of either B-raf mRNA transcript of approximately 30% or greater were considered active. According to this criterion, oligonucleotides 13722, 13724, 13726, 13727, 13728, 13730, 13732, 13733, 13736, 13739, 13740, 13741, 13742, 13743, 14135, 14136, 14138 and 14144 were found to be active. These sequences (SEQ ID NO: 3, 5, 7, 8, 9, 11, 13, 14, 17, 20, 21, 22, 32, 36, 33, 31, 29 and 23, respectively) are therefore preferred. Of these, oligonucleotides 13727, 13730, 13740, 13741, 13743 and 14144 (SEQ ID NO: 8, 11, 21, 22, 36 and 23, respectively) showed 40–50% inhibition of one or both B-raf transcripts in at least one assay. These sequences are therefore more preferred. In one of the two assays, ISIS 14144 (SEQ ID NO: 23) reduced levels of both transcripts by 50–60% and ISIS 13741 (SEQ ID NO: 22) reduced both transcripts by 65–70%. These two sequences are therefore highly preferred.

Figure 2B:
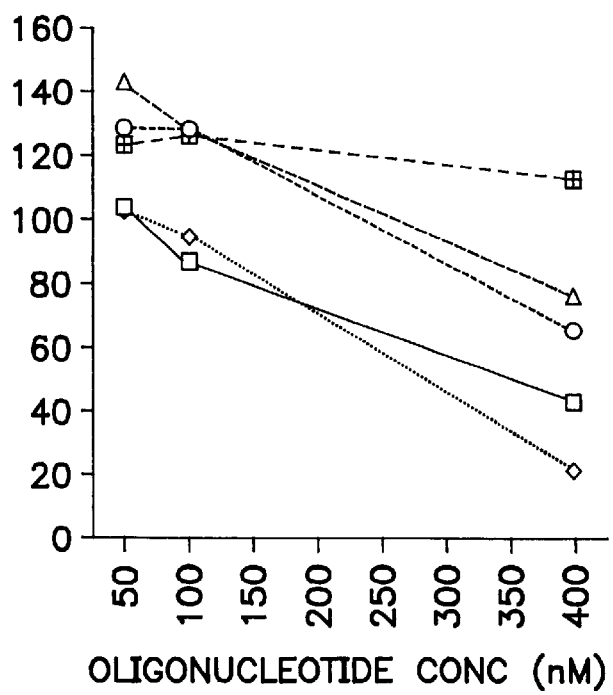

Dose response experiments were done in both T24 cells and A549 cells for the two most active oligonucleotides, ISIS 13741 and ISIS 14144 (SEQ ID NO: 22 and 23), along with mismatch control sequences having 1, 3 or 5 mismatches of the ISIS 13741 sequence (SEQ ID NO: 22). FIG. 2 shows dose-response curves for reduction of B-raf mRNA levels in A549 cells by these oligonucleotides (all are phosphorothioate oligodeoxynucleotides) after a 4-hour treatment in the presence of lipofectin. Results are normalized to G3PDH and expressed as a percent of control. FIG. 2A shows a dose-response curve for inhibition of the upper B-raf transcript. ISIS 13741 and 14144 had almost identical activity in this assay, with IC50s between 250 and 300 nM. The mismatch controls had no activity (ISIS 14531) or slight activity, with a maximum inhibition of less than 20% at the 400 nM dose (ISIS 14530, ISIS 14529). FIG. 2B shows a dose-response curve for inhibition of the lower B-raf transcript in A549 cells. Against the lower transcript, ISIS 13741 and ISIS 14144 had IC50s of approximately 350 and 275 nM, respectively in this assay, with the mismatch controls never achieving 50% inhibition at concentrations up to 400 nM. Therefore, ISIS 13741 and 14144 are preferred.

Figure 3A:
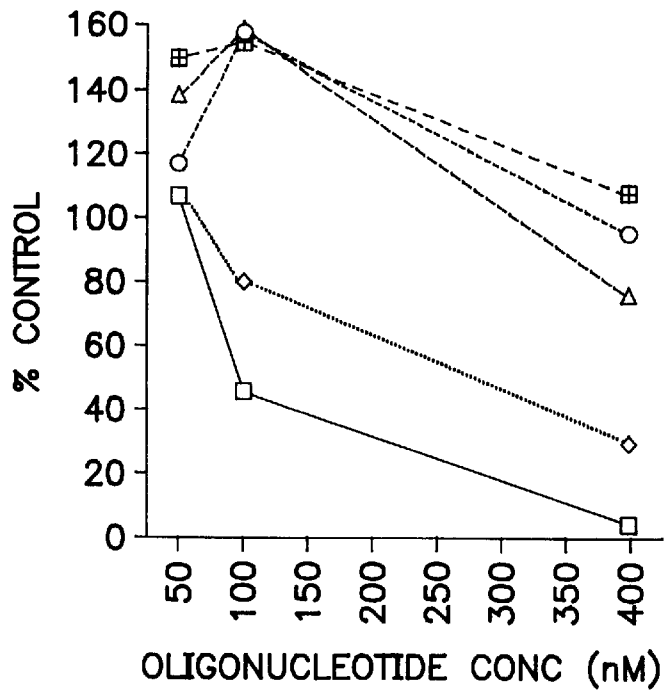
FIGS. 3A and 3B are a set of line graphs showing dose-response curves for reduction of B-raf mRNA levels in human T24 tumor cells by phosphorothioate oligodeoxynucleotides 13741 (open squares), 14144 (diamonds), 14529 (circles), 14530 (triangles) and 14531 (crosshatched squares) after a 4-hour treatment in the presence of lipofectin. Results are normalized to G3PDH and expressed as a percent of control.
Figure 3B:
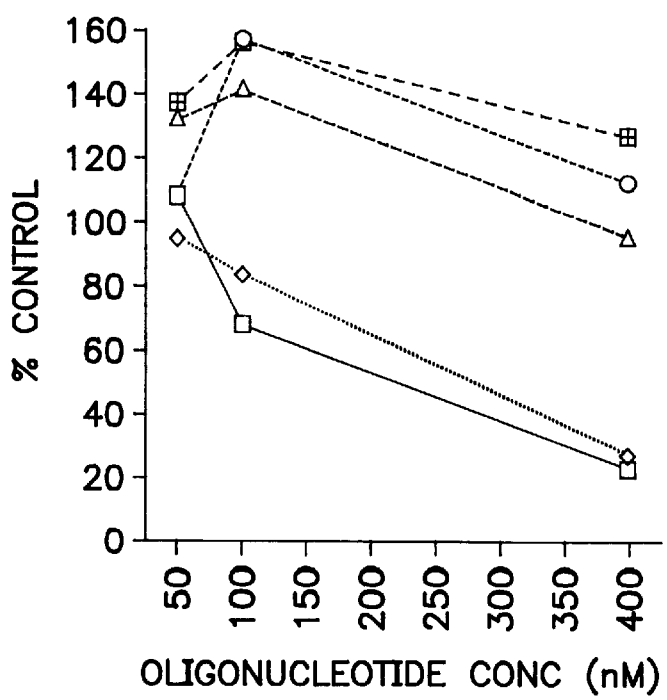

FIG. 3 shows dose-response curves for reduction of B-raf mRNA levels in T24 cells by these oligonucleotides (all are phosphorothioate oligodeoxynucleotides) after a 4-hour treatment in the presence of lipofectin. Results are normalized to G3PDH and expressed as a percent of control. FIG. 3A shows a dose-response curve for inhibition of the upper B-raf transcript. ISIS 13741 and 14144 were again most active, with IC50s of approximately 100 nM and 275 nM, respectively, in this assay. The mismatch controls 14529 and 14531 had no activity, and the mismatch control 14530 achieved a maximum reduction of raf mRNA of approximately 20% at a 400 nM dose. FIG. 3B shows a dose-response curve for inhibition of the lower B-raf transcript in T24 cells. Against the lower transcript, ISIS 13741 had an IC50 of approximately 100–125 nM and ISIS 14144 had an IC50 of approximately 250 nM in this assay, with the mismatch controls completely inactive. Therefore ISIS 13741 and 14144 are preferred.

2'-Methoxyethoxy (2'-MOE) oligonucleotides targeted to B-raf:

The oligonucleotides shown in Table 2 were synthesized. Nucleotides shown in bold are 2'-MOE. 2'-MOE cytosines are all 5-methylcytosines. For backbone linkage, "s" indicates phosphorothioate (P=S) and "o" indicates phosphodiester (P=O).

TABLE 2

2'-MOE oligonucleotides targeted to human B-raf (bold = 2'-MOE)

| ISIS# | Sequence/modification | SEQ ID NO: |
|---|---|---|
| 13741 | CsTsGsCsCsTsGsGsAsTsGsGsGsTsGsTsTsTsT | 22 |
| 15339 | CsTsGsCsCsTsGsGsAsTsGsGsGsTsGsTsTsTsT | 22 |
| 15340 | CoToGoCoCoToGoGoAoToGsGsGsTsGsTsTsTsT | 22 |
| 15341 | CsTsGsCsCsTsGsGsAsTsGsGsGsTsGsTsTsTsT | 22 |
| 15342 | CoToGoCoCsTsGsGsAsTsGsGsGsTsGoToToToT | 22 |
| 15343 | CsTsGsCsCsTsGsGsAsToGoGoGoToGoToToToT | 22 |
| 15344 | CsTsGsCsCsTsGsGsAsTsGsGsGsTsGsTsTsTsT | 22 |

Figure 4A:
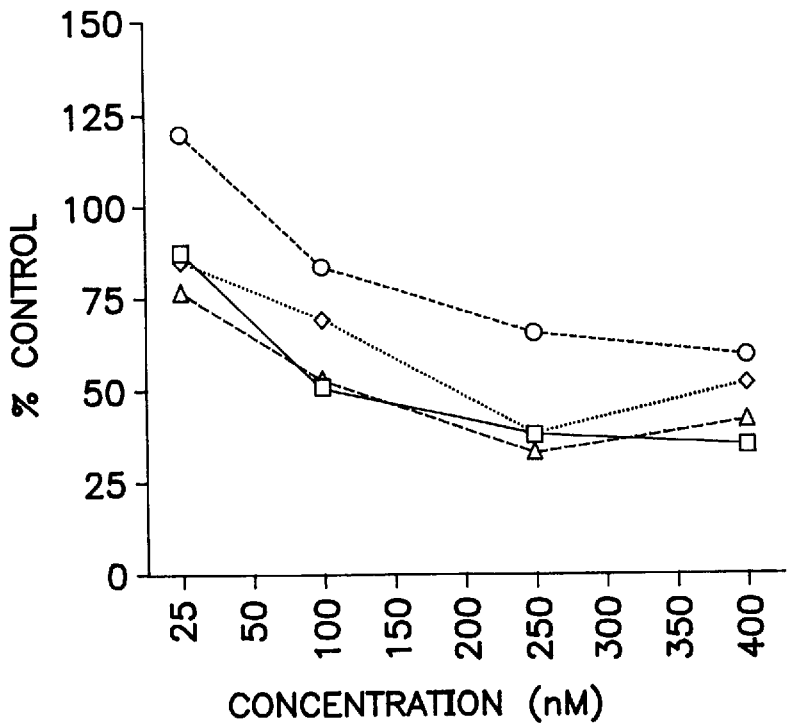
FIGS. 4A and 4B are a set of line graphs showing dose-response curves for reduction of B-raf mRNA levels in human T24 tumor cells by phosphorothioate oligodeoxynucleotides 13741 (squares) and 2'-methoxyethoxy oligonucleotides 15341 (diamonds), 15342 (circles) and 15344 (triangles) after a 4-hour treatment in the presence of lipofectin. Results are normalized to G3PDH and expressed as a percent of control.
Figure 4B:
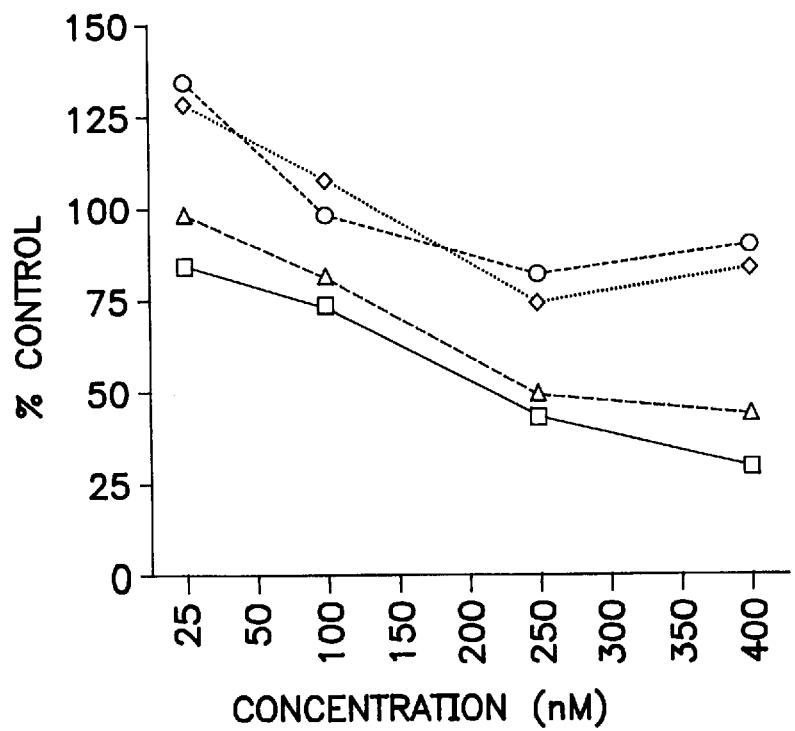

These oligonucleotides were tested for their ability to reduce B-raf mRNA levels in T24 cells. Dose response curves for ISIS 13741, 15341, 15342 and 15344 are shown in FIG. 4A. FIG. 4A shows the effect of these oligonucleotides on the lower B-raf transcript and FIG. 4B shows the effect on the upper transcript. Against the lower transcript, ISIS 13741 (P=S deoxy) and ISIS 15344 (P=S deoxy/MOE) had IC50s of approximately 250 nM. The other two compounds tested, ISIS 15341 and 15342, did not achieve 50% inhibition at doses up to 400 nM. Against the upper transcript, ISIS 13741 and 15344 demonstrated IC50s of approximately 150 nM, ISIS 15341 demonstrated an IC50 of approximately 200 nM and ISIS 15342 did not achieve 50% reduction at doses up to 400 nM. Based on these results, ISIS 15341, 13741 and 15344 are preferred. The following examples are provided for illustrative purposes only and are not intended to limit the invention.

EXAMPLES

Example 1

Synthesis and Characterization of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va. 2'-fluoro oligonucleotides were synthesized as described in Kawasaki et al., *J. Med. Chem.* 1993, 36, 831–841. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl-(DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

Synthesis of 2'-deoxy-2'-fluorouridine was accomplished by the modification of a literature procedure in which 2,2'-anhydro-1-β-D-arabinofuranosyluracil was treated with 70% hydrogen fluoride-pyridine. Standard procedures were used to obtain the 5'-DMT and 5'-DMT-3'phosphoramidites. 2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3'phosphoramidites.

2'-(2-methoxyethyl)-modified amidites are synthesized according to Martin, P., *Helv. Chim. Acta* 1995, 78,486–504. For ease of synthesis, the last nucleotide was a deoxynucleotide. 2'-O—$CH_2CH_2OCH_3$— cytosines may be 5-methyl cytosines.

Synthesis of 5-Methyl cytosine monomers:
2,2'-Anhydro[1-(β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5-methylcytidine-3'-amidite:

$N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., 1993, *Nucl. Acids Res.* 21:3197–3203) using commercially available phosphoramidites (Glen Research, Sterling Va. or ChemGenes, Needham Mass.).

Oligonucleotides having methylene (methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.* 1995, 28, 366–374. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller). Peptide-nucleic acid (PNA) oligomers are synthesized according to P. E. Nielsen et al., *Science* 1991, 254, 1497).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., 1991, *J. Biol. Chem.*, 266:18162–18171. Results obtained with HPLC-purified material were similar to those obtained with non-HPLC purified material.

Example 2

Northern Blot Analysis of Inhibition of B-raf mRNA Expression

The human urinary bladder cancer cell line T24 and the human lung tumor cell line A549 were obtained from the American Type Culture Collection (Rockville Md.). T24 cells were grown in McCoy's 5A medium with L-glutamine and A549 cells were grown in DMEM low glucose medium (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 μl DOTMA per 100 nM oligonucleotide. Oligonucleotide with lipofectin was then added to the desired concentration. After 4 hours of treatment, the medium was replaced with appropriate medium (McCoy's or DMEM low glucose). Cells were harvested 24 to 72 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to a $^{32}$P-labeled B-raf cDNA probe or G3PDH probe as a control. The human B-raf cDNA probe was cloned by PCR using complementary oligonucleotide primers after reverse transcription of total RNA. Identity of the B-raf cDNA was confirmed by restriction digestion and direct DNA sequencing. RNA was quantitated using a Phosphorimager (Molecular Dynamics, Sunnyvale, Calif.).

Example 3

Antisense Inhibition of Cell Proliferation

T24 cells are treated on day 0 for two hours with various concentrations of oligonucleotide and lipofectin (50 nM oligonucleotide in the presence of 2 μg/ml lipofectin; 100 nM oligonucleotide and 2.5 μg/ml lipofectin; 250 nM oligonucleotide and 6 μg/ml lipofectin or 500 nM oligonucleotide and 12.5 μg/ml lipofectin). On day 1, cells are treated for a second time at desired oligonucleotide concentration for two hours. On day 2, cells are counted.

Example 4

Effect of ISIS 13741 on T24 Human Bladder Carcinoma Tumor Xenografts in Nude Mice 5×10$^6$ T24 cells are implanted subcutaneously in the right inner thigh of nude mice. Oligonucleotides (ISIS 13741 and an unrelated control phosphorothioate oligonucleotide suspended in saline) are administered three times weekly beginning on day 4 after tumor cell inoculation. A saline-only control is also given. Oligonucleotides are given by intraperitoneal injection. Oligonucleotide dosage is 25 mg/kg. Tumor size is measured and tumor volume is calculated on the eleventh, fifteenth and eighteenth treatment days.

Example 5

Effect of ISIS 13741 on MDA-MB 231 Human Breast Carcinoma Tumor Xenografts in Nude Mice 5×10$^6$ MDA-MB 231 cells are implanted subcutaneously in the right inner thigh of nude mice. Oligonucleotides (ISIS 13741 and an unrelated control phosphorothioate oligonucleotide suspended in saline) are administered once daily beginning on day 10 after tumor cell inoculation. A saline-only control is also given. Oligonucleotides are given by intravenous injection at a dosage of 0.6 mg/kg or 6.0 mg/kg. Tumor size is measured and tumor volume is calculated on days 10, 13, 16, 20, 23 and 27 following tumor cell inoculation.

For intraperitoneal oligonucleotide administration, oligonucleotides are administered once daily beginning on day 10 after tumor cell inoculation. A saline-only control is also given. Oligonucleotides are given by intraperitoneal injection at a dosage of 0.6 mg/kg or 6.0 mg/kg. Tumor size is measured and tumor volume is calculated on days 10, 13, 16, 20, 23 and 27 following tumor cell inoculation.

Example 6

Effect of ISIS 13741 on Colo 205 Human Colon Carcinoma Tumor Xenografts in Nude Mice $5 \times 10^6$ Colo 205 cells are implanted subcutaneously in the right inner thigh of nude mice. Oligonucleotides (ISIS 13741 and an unrelated control phosphorothioate oligonucleotide suspended in saline) are administered once per day beginning on day 5 after tumor cell inoculation. A saline-only control is also given. Oligonucleotides are given by intravenous injection. Oligonucleotide dosage is 6 mg/kg. Tumor size is measured and tumor volume is calculated on days 5, 8, 11, 14, 18, 22 and 25 after tumor inoculation.

Example 7

Diagnostic Assay for raf-associated Tumors Using Xenografts in Nude Mice

Tumors arising from raf expression are diagnosed and distinguished from other tumors using this assay. A biopsy sample of the tumor is treated, e.g., with collagenase or trypsin or other standard methods, to dissociate the tumor mass. $5 \times 10^6$ tumor cells are implanted subcutaneously in the inner thighs of two or more nude mice. Antisense oligonucleotide (e.g., ISIS 13741) suspended in saline is administered to one or more mice by intraperitoneal injection three times weekly beginning on day 4 after tumor cell inoculation. Saline only is given to a control mouse. Oligonucleotide dosage is 25 mg/kg. Tumor size is measured and tumor volume is calculated on the eleventh treatment day. Tumor volume of the oligonucleotide-treated mice is compared to that of the control mouse. The volume of raf-associated tumors in the treated mice are measurably smaller than tumors in the control mouse. Tumors arising from causes other than raf expression are not expected to respond to the oligonucleotides targeted to raf and, therefore, the tumor volumes of oligonucleotide-treated and control mice are equivalent.

Example 8

Detection of raf Expression

Oligonucleotides are radiolabeled after synthesis by $^{32}$P labeling at the 5' end with polynucleotide kinase. Sambrook et al., *Molecular Cloning. A Laboratory Manual*, Cold Spring Harbor Laboratory Press, 1989, Volume 2, pg. 11.31–11.32. Radiolabeled oligonucleotides are contacted with tissue or cell samples suspected of raf expression, such as tumor biopsy samples, under conditions in which specific hybridization can occur, and the sample is washed to remove unbound oligonucleotide. Radioactivity remaining in the sample indicates bound oligonucleotide and is quantitated using a scintillation counter or other routine means.

Radiolabeled oligonucleotides of the invention are also used in autoradiography. Tissue sections are treated with radiolabeled oligonucleotide and washed as described above, then exposed to photographic emulsion according to standard autoradiography procedures. The emulsion, when developed, yields an image of silver grains over the regions expressing raf. The extent of raf expression is determined by quantitation of the silver grains.

Analogous assays for fluorescent detection of raf expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of oligonucleotide and biological sample is carried out as described for radiolabeled oligonucleotides except that instead of a scintillation counter, a fluorimeter or fluorescence microscope is used to detect the fluorescence which indicates raf expression.

Example 9

A549 Xenografts

A549 cells are obtained from the American Type Culture Collection (Bethesda Md.) and grown in T-75 flasks until 65–75% confluent. $5 \times 10^6$ A549 cells are implanted subcutaneously in the inner thigh of nude mice. Oligonucleotides (ISIS 13741 and a scrambled raf control phosphorothioate oligonucleotide, ISIS 10353) suspended in saline are administered once daily by intravenous injection at doses ranging from 0.006 to 6.0 mg/kg. Resulting tumors are measured on days 9, 12, 17 and 21 and tumor volumes are calculated.

Example 10

U-87 Human Glioblastoma Cell Culture and Subcutaneous Xenografts into Nude Mice Ahmad et al. disclose that transfection of the human glioblastoma cell line, U-87, with vectors expressing antisense RNA to PKCα inhibits growth of the glioblastoma cells in vitro and in vivo. Ahmad et al., 1994, *Neurosurg.* 35:904–908. The U-87 human glioblastoma cell line is obtained from the ATCC (Rockville Md.) and maintained in Iscove's DMEM medium supplemented with heat-inactivated 10% fetal calf serum. Nude mice are injected subcutaneously with $2 \times 10^7$ cells. Mice are injected intraperitoneally with oligonucleotide at dosages of either 2 mg/kg or 20 mg/kg for 21 consecutive days beginning 7 days after xenografts were implanted. Tumor volumes are measured on days 14, 21, 24, 31 and 35 and compared to volumes obtained after treatment with saline or sense oligonucleotide control.

Example 11

Intracerebral U-87 Glioblastoma Xenografts in Nude Mice

U-87 cells are implanted in the brains of nude mice. Mice were treated via continuous intraperitoneal administration of antisense oligonucleotide (20 mg/kg), control sense oligonucleotide (20 mg/kg) or saline beginning on day 7 after xenograft implantation. Survival (in days) of treated mice are compared to survival of untreated or control-treated mice.

What is claimed is:

1. An oligonucleotide 8 to 50 nucleotides in length which is targeted to base pairs 1520 through 1545, 2306 through 2354 or 2372 through 2408 of a nucleic acid encoding human B-raf and which inhibits B-raf expression.

2. The oligonucleotide of claim 1 which has at least one modified backbone linkage.

3. The oligonucleotide of claim 1 wherein at least one of the nucleotide units of the oligonucleotide is modified at the 2' position of the sugar moiety.

4. The oligonucleotide of claim 1 in a pharmaceutically acceptable carrier.

5. The oligonucleotide of claim 1 which is a chimeric oligonucleotide.

6. An oligonucleotide targeted to a nucleic acid encoding human B-raf, which inhibits B-raf expression and which comprises SEQ ID NO: 3, 5, 7, 8, 9, 11, 13, 14, 17, 20, 21, 22, 32, 36, 33, 31, 29 or 23.

* * * * *